United States Patent [19]
Vogel et al.

[11] 3,931,251
[45] Jan. 6, 1976

[54] PROCESS FOR THE MANUFACTURE OF 1-NITROANTHRAQUINONE

[75] Inventors: Axel Vogel, Cologne; Reinold Schmitz, Blecher, both of Germany

[73] Assignee: Bayer Aktiengesellschaft, Leverkusen-Bayerwerk, Germany

[22] Filed: Oct. 5, 1973

[21] Appl. No.: 403,765

[30] Foreign Application Priority Data
Oct. 6, 1972 Germany............................ 2248990

[52] U.S. Cl. .................................................. 260/369
[51] Int. Cl.² ........................................... C07C 79/37
[58] Field of Search ................................... 260/369

[56] References Cited
UNITED STATES PATENTS
2,302,729  11/1942  Whelen ............................... 260/369
3,786,073  1/1974  Frey et al. ........................... 260/369
3,798,244  3/1974  Mueller et al. ...................... 260/369

OTHER PUBLICATIONS

Reichel, et al., as cited in *Chem. Abstracts* 70, p. 38877z, (1969).

*Primary Examiner*—Lorraine A. Weinberger
*Assistant Examiner*—E. Jane Skelly
*Attorney, Agent, or Firm*—Plumley & Tyner

[57] ABSTRACT

Preparation of very pure 1-nitroanthraquinone by heating 1-nitroanthraquinone which contains dinitroanthraquinone with the aqueous solution of a salt of sulphurous acid in the presence of an inert organic solvent.

9 Claims, No Drawings

PROCESS FOR THE MANUFACTURE OF 1-NITROANTHRAQUINONE

The present invention relates to an improved process for the manufacture of 1-nitroanthraquinone which is practically free of dinitroanthraquinone, from 1-nitroanthraquinone which contains dinitroanthraquinone, by heating with salts of sulphurous acid in an aqueous medium, which is characterised in that the reaction with the salt of sulphurous acid is carried out in the presence of an inert organic solvent.

By 1-nitroanthraquinone containing dinitroanthraquinone there is here understood a 1-nitroanthraquinone essentially contaminated with 2-nitroanthraquinone and 1,5-, 1,6-, 1,7- and 1,8-dinitroanthraquinone, such as is obtained on nitration of anthraquinone.

Possible salts of sulphurous acid are especially the alkali metal sulphites, for example sodium sulphite or potassium sulphite, or ammonium sulphite, and also the acid salts such as sodium bisulphite, or sulphur dioxide in combination with bases or compounds giving a basic reaction.

The amount and concentration of the salts of sulphurous acid can vary within wide limits. In general, 0.1–2 mols, preferably 0.2–1.5 mols, of sulphite are employed per mol of 1-nitroanthraquinone. The concentration of the sulphite solution is generally about 0.5 - 20% by weight, preferably 1–15% by weight.

Inert organic solvents which can be used are both water-miscible and water-immiscible solvents, the latter being preferred.

As examples of solvents which can be used for the process according to the invention there may be mentioned aromatic and araliphatic hydrocarbons from the benzene and naphthalene series with up to 30, preferably up to 20, C atoms, which can be substituted in the nucleus, for example by halogen, (fluorine, chlorine, bromine or iodine), nitro, sulphone, ether, thioether, keto and/or carboalkoxy groups; additionally, aliphatic and alicyclic hydrocarbons with up to 30, preferably with up to 20, C atoms, which can be substituted, for example by halogen (fluorine, chlorine, bromine or iodine) or the nitro, sulphone, sulphoxide, ether, thioether, hydroxyl, carbonyl, carboxyl and/or carboalkoxy or carboaryloxy group.

The following may be mentioned as examples: benzene, toluene, the isomeric o-, m- and p-xylenes, ethylbenzene, cumene, n-propylbenzene, pseudocumene, mesitylene, p-cymene, durene, the isomeric diethylbenzenes and diisopropylbenzenes, tert.-butylbenzene, tert.-butyltoluene, tert.-butylxylene, triisopropylbenzene, isododecylbenzene, diphenylmethane, ditolylmethane, diphenylethane, α-methylstyrene, stilbene, dihydrostilbene, indene, indane, naphthalene, tetralin, methylnaphthalene, methyltetralin, ethylnaphthalene, isopropylnaphthalene, diisopropylnaphthalene, isooctylnaphthalene and isododecylnaphthalene; pentane, hexane, heptane, octane, nonane, decane, undecane, dodecane, cyclopentane, cyclohexane, cyclooctane, cyclodecane and decalene.

The list of examples of course also covers, in addition to the compounds mentioned, the straight-chain or branched isomers and the alkyl-substituted cycloaliphatic and aromatic compounds.

As examples of hydrocarbons substituted by heteroatoms there may be mentioned: chlorobenzene, o-, m- and p-dichlorobenzene, 1,2,3- and 1,2,4-trichlorobenzene, o-, m- and p-chlorotoluene, benzotrichloride, the isomeric dichlorotoluenes, chloroxylenes, dichloroxylenes and chlorocumenes; also α- and β-chloronaphthalene and chloromethylnaphthalene; bromobenzene, bromotoluene, bromonaphthalene and chlorobromobenzene; carbon tetrachloride, difluorodichloromethane, difluorodibromomethane and perfluoromethylcyclohexane; nitrobenzene, nitrotoluene, nitronaphthalene, and nitromethane; anisole, chloroanisole, bromoanisole, phenetol, veratrol, and hydroquinone dimethyl ether; diethyl ether, diisopropyl ether, di-n-butyl ether, di-isobutyl ether, dioxane and tetrahydrofurane; ethylene glycol and its monomethyl, dimethyl, monoethyl, diethyl, isopropyl and butyl ethers, diethylene glycol and its methyl, dimethyl, ethyl, diethyl, isopropyl and butyl ethers, propylene glycol, methanol, ethanol, propanol, butanol and pentanol; dimethylsulphone and tetramethylenesulphone.

Of course, mixtures of different solvents can also be used.

The amount of the organic solvent can be varied within wide limits. In general, 0.01 part by volume of solvent per part by weight of 1-nitroanthraquinone already suffices to achieve a distinct effect. Preferably, 0.05–40, especially 0.1–10, parts by volume of organic solvent are used per part by weight of 1-nitroanthraquinone.

It is not necessary for the crude 1-nitroanthraquinone to be completely dissolved in the organic solvent. The reaction is preferably carried out in such a way that the 1-nitroanthraquinone is wholly or partially suspended in the organic solvents.

The reaction mixture can additionally contain foreign salts, for example salts which originate from neutralisation of the acids used in the nitration, such as sodium nitrate, sodium sulphate, sodium fluoride, sodium hydrogen phosphate or sodium phosphate or salts which are added to produce a particular pH-value.

Furthermore, the reaction mixture can contain surface-active substances such as emulsifiers, wetting agents, anti-foaming agents and similar additives. The addition of such surface-active compounds is particularly advantageous if severe foaming is to be prevented or separation of the aqueous and organic phase, or better wetting of the crystals by the aqueous phase, are to be favoured.

The reaction is generally carried out at a pH-value above 8, preferably at pH 9–12. The pH-value is adjusted, for example, by adding bases such as sodium hydroxide solution, potassium hydroxide solution or alkali metal carbonate or acids such as hydrochloric acid, sulphuric acid, phosphoric acid, sulphurous acid or sulphur dioxide, or by means of salts which maintain a certain pH-value through their buffer action; preferably, the reaction mixture is left at the pH-value which results from the reaction components due to hydrolysis and reaction.

The reaction temperature can be varied over a wide range. In general, the reaction temperature is kept at between 75°C and 150°C, preferably between 80°C and 130°C, and especially between 85°C and 110°C.

The process according to the invention can be carried out at normal, lowered or elevated pressure. Working under elevated pressure may at times be absolutely essential in order to reach the chosen reaction temperature. Preferably, the reaction is carried out under normal pressure or under the autogenic pressure of the reaction mixture.

In general, the process according to the invention is carried out by dissolving or suspending the 1-nitroanthraquinone in water and/or the organic solvent or initially introducing the neutralised nitration batch, if necessary after distillation or decantation of the undesired solvents originating from the nitration, adding the particular salt of sulphurous acid, or sulphur dioxide, in bulk or as an aqueous solution, all at once, batchwise or continuously, optionally with simultaneous addition of sodium hydroxide solution, adding the organic solvent before, simultaneously with or after the addition of the sulphite, again all at once, batchwise or continuously, and maintaining the reaction mixture at the chosen reaction temperature for several hours, whilst stirring. The foreign salts, bases, acids or surface-active compounds which are used optionally are added prior to or simultaneously with the reactants or in the course of the reaction or subsequently, all at once, batchwise or continuously.

It can also be of advantage first to react the 1-nitroanthraquinone with a part or the whole of the amount of sulphite, without organic solvent, and only after a certain reaction time to add the organic solvent all at once, batchwise or continuously and, where relevant, subsequently to add the remaining amount of sulphite and then to complete the reaction.

A further advantageous embodiment consists of heating 1-nitroanthraquinone initially with the organic solvent, in the absence of sulphite, and optionally in the presence of water, to temperatures of up to about 240°C, preferably up to about 200°C and especially up to about 160°C, to cool the mixture again to the reaction temperature after some time, and then to add the sulphite, water and, if appropriate, further organic solvent and to carry out the reaction as described.

The purified, sparingly soluble 1-nitroanthraquinone can be isolated in various ways; for example, the 1-nitroanthraquinone can be isolated at temperatures between 5°C and 150°C, preferably between 10°C and 110°C, by filtration, decantation or centrifuging, if appropriate after removal of the organic phase, and can be washed with an organic solvent and/or water and dried if appropriate. This preferred working-up technique is particularly advantageous if the nitration product employed still contains anthraquinone, since the anthraquinone can then be removed simultaneously with the mother liquor. It is however also possible first to distil off the organic solvent and then to isolate the sparingly soluble 1-nitroanthraquinone from the aqueous phase according to the known methods.

The purified 1-nitroanthraquinone manufactured according to the invention can be directly reduced to 1-aminoanthraquinone without isolation, optionally after removal of the organic solvent; sodium sulphide, for example, is used for the reduction. The 1-aminoanthraquinone can then be isolated in the usual manner by filtering, centrifuging or decanting the batch or, if appropriate, evaporating the organic phase.

The process according to the invention can be carried out discontinuously, for example in a stirred kettle, or continuously, for example in a kettle cascade, in an interval tube, in a circulation installation or in similar apparatuses.

1-Nitroanthraquinone is an important industrial intermediate product for the manufacture of 1-aminoanthraquinone, the starting product for numerous anthraquinone dyestuffs.

U.S. Pat. No. 2,302,729 has already disclosed a process for the purification of crude 1-nitroanthraquinone in which the crude 1-nitroanthraquinone is heated for several hours to 100°C with 0.2–0.5 mol of sodium sulphite in an aqueous medium. In the course thereof, the anthraquinones containing β-nitro groups are in particular supposed to be converted into water-soluble compounds. However, the process suffers from a series of disadvantages. Thus, the removal of the by-products containing β-nitro groups, especially 2-nitroanthraquinone and 1,6- and 1,7-dinitroanthraquinone, leaving residual contents of, in each case, about 1 per cent by weight, is rather unsatisfactory for present-day purity criteria. Above all, however, the removal of the α,α'-dinitroanthraquinones, that is to say 1,5- and 1,8-dinitroanthraquinone, and amongst these especially the removal of 1,5-dinitroanthraquinone, takes place, according to this process, to a completely inadequate extent, as a result of which this process is unsuitable for purifying 1-nitroanthraquinone with a view to the manufacture of anthraquinone dyestuffs.

German Offenlegungsschrift (German Published Specification) 2,206,960 proposes to increase the purification effect by using substantially larger amounts of sodium sulphite simultaneously with higher sulphite ion concentration, at least 0.5 part by weight of sodium sulphite being employed per part by weight of crude 1-nitroanthraquinone, corresponding to about 1 mol, preferably about 1.5–3 mols, of sodium sulphite per mol of 1-nitroanthraquinone. However, this process again does not make it possible, without a separate preliminary purification of the crude nitration product, to reduce the residual content of the by-products below 10% by weight and to produce an even approximately pure 1-nitroanthraquinone. Even if a preliminary purification is introduced into the process, which however is technically very involved and associated with losses in yield, and is therefore uneconomical, this process still leaves a residual content of at least 3% by weight of the dinitroanthraquinones which interfere greatly with further conversion to anthraquinone dyestuffs.

The process according to the invention offers a number of important advantages over the process according to the state of the art. Thus, as compared to the state of the art, the residual content of 1,5-dinitroanthraquinone, in particular, can be substantially reduced. At the same time, the residual contents of the remaining impurities, such as 1,6- and 1,7-dinitroanthraquinone, but especially 1,8-dinitroanthraquinone and 2-nitroanthraquinone and anthraquinone can, by the process according to the invention, in part be reduced to below the limit of analytical detection, so that overall, as compared to the state of the art, the quality of the 1-nitroanthraquinone is substantially improved and 1-nitroanthraquinone of a degree of purity of 98–99% is directly obtained.

EXAMPLE 1

85 ml of 100% strength by weight sulphuric acid are slowly added dropwise, over the course of about 3 hours, to a mixture of 250 g of anthraquinone (99% pure), 200 ml of methylene chloride and 65.5 ml of 98% strength by weight nitric acid in a three-neck flask with fitted stirrer, reflux condenser and dropping funnel, whilst stirring at the reflux temperature. The batch is stirred for a further 4 hours at the same temperature and then poured into 1,000 ml of water, and the methylene chloride is distilled off. The aqueous suspension which remains is filtered and the filter cake is washed with water until neutral. The dried filter residue (300 g) is stirred with 90 g of sodium sulphite, 2,400 ml of water and 1,200 ml of chlorobenzene for 6 hours in an autoclave at 105°C. The mixture is cooled to 20°C and the precipitate is filtered off at this temperature and washed successively with 75 ml of chlorobenzene and then with water. After drying, 206 g of 1-nitroanthraquinone having the composition indicated in Table A are obtained. A further fraction of 19 g of 1-nitoanthraquinone remains in solution in the mother liquor, which can be re-used for the next nitration. The total yield is 73% of theory.

EXAMPLE 2

50 g of a crude 1-nitroanthraquinone manufactured according to Example 1 are stirred, according to U.S. Pat. No. 2,302,729, with 10 g of sodium sulphite and 500 ml of water for 6 hours at the reflux temperature. After filtration, washing and drying, 40.4 g of 1-nitroanthraquinone of the composition indicated in Table A are isolated (representing 71% of theory, relative to anthraquinone employed).

EXAMPLE 3

50 G of a crude 1-nitroanthraquinone manufactured according to Example 1 are treated, in accordance with German Offenlegungsschrift (German Published Specification) 2,206,960, with 30 g of sodium sulphite in 400 ml of water. After filtration, washing and drying, 34.6 g of 1-nitroanthraquinone of the composition indicated in Table A are obtained (= 63% of theory, relative to anthraquinone employed).

contains a further 20 g of 1-nitroanthraquinone so that the total yield is 73% of theory.

EXAMPLE 5

250 G of anthraquinone are nitrated as in Example 1. The dried nitration product is heated with 90 g of sodium sulphite, 1,200 ml of water and 1,200 ml of chlorobenzene to 105°C for 6 hours. The mixture is cooled to 20°C and the precipitate is filtered off at this temperature and washed initially with twice 120 ml of chlorobenzene and then with water. The yield of dry material is 203 g of 96% strength by weight 1-nitroanthraquinone. The chlorobenzene mother liquor contains a further 15 g of 1-nitroanthraquinone.

EXAMPLE 6

250 G of anthraquinone are nitrated as in Example 1. The dry nitration product is heated for 6 hours to 105°C with 90 g of sodium sulphite, 600 ml of water and 1,200 ml of chlorobenzene. The mixture is cooled to 20°C and the precipitate is filtered off and washed with twice 120 ml of chlorobenzene and then with water. The yield of dry material is 190 g of 96% strength by weight 1-nitroanthraquinone. The organic mother liquor contains a further 15 g of 1-nitroanthraquinone.

EXAMPLE 7

50 G of an anthraquinone nitration product manufactured according to Example 1 are stirred for 6 hours with 200 ml of chlorobenzene, 400 ml of water and 7.5 g of sodium sulphite at 130°C. The precipitate is filtered off at 20°C, washed with 40 ml of chlorobenzene Table A

| Example No. | I | II | III | IV | V | VI | VII | VIII |
|---|---|---|---|---|---|---|---|---|
| 1 | 0.25 | 98 | <0.25 | 1.0 | 0.3 | 0.2 | 0.1 | 0.1 |
| 2 | ~3 | 88 | 2.2 | 2.6 | 0.8 | 0.8 | 1.0 | 1.1 |
| 3 | ~3 | 89 | 1.3 | 2.8 | 0.7 | 0.6 | 0.9 | 1.1 |
| 4 | 0.5 | 97 | 0.25 | 1.4 | 0.1 | 0.2 | 0.2 | 0.2 |
| 5 | 0.5 | 96 | 0.5 | 1.5 | 0.3 | 0.2 | 0.4 | 0.2 |
| 6 | 0.5 | 96 | 0.5 | 1.4 | 0.2 | 0.2 | 0.2 | 0.1 |
| 9 | 0.25 | 98 | <0.25 | 0.9 | 0.2 | 0.2 | 0.2 | 0.1 |
| 10 | 0.25 | 97 | <0.25 | 1.1 | 0.3 | 0.2 | 0.3 | 0.3 |
| 12 | 0.25 | 99 | 0.25 | 0.1 | 0.1 | 0.1 | — | — |
| 30 | 0.25 | 97 | <0.25 | 1.4 | 0.2 | 0.2 | 0.4 | 0.4 |
| 32 | <0.25 | 98 | <0.25 | 0.6 | 0.3 | 0.2 | 0.3 | 0.2 |
| 33 | 0.5 | 98 | 0.25 | 0.8 | 0.2 | 0.2 | 0.2 | 0.1 |
| 34 | ~3 | 90 | 1.2 | 2.8 | 0.7 | 0.6 | 0.9 | 1.1 |

I = % by weight of anthraquinone
II = % by weight of 1-nitroanthraquinone
III = % by weight of 2-nitroanthraquinone
IV = % by weight of 1,5-dinitroanthraquinone
V = % by weight of 1,6-dinitroanthraquinone
VI = % by weight of 1,7-dinitroanthraquinone
VII = % by weight of 1,8-dinitroanthraquinone
VIII = % by weight of hydroxynitroanthraquinones

EXAMPLE 4

250 G of anthraquinone are nitrated as in Example 1. The dried nitration product is heated with 90 g of sodium sulphite, 2,400 ml of water, 1.5 g of di-sec.-butyl naphthalenesulphonate and 1,200 ml of toluene for 4 hours in an autoclave to 105°C. The mixture is then cooled to 60°C in a separating vessel and at this temperature the organic phase is siphoned off. The aqueous suspension is filtered and the filter residue is washed with water and dried. The yield is 207 g and the content of 1-nitroanthraquinone is 97% by weight, corresponding to 66% of theory. The organic phase and then with water and dried. 36.1 g of 93% strength by weight 1-nitroanthraquinone are obtained, corresponding to 68% of theory. The content of 1,5-dinitroanthraquinone is 1.9% by weight and the content of anthraquinone is 0.25% by weight. The total yield is 74% of theory.

EXAMPLE 8

50 G of an anthraquinone nitration product manufactured according to Example 1 are stirred for 6 hours with 200 ml of chlorobenzene, 400 ml of water and 7.5 g of sodium sulphite at 140°C. The precipitate is filtered off at 20°C, washed with 40 ml of chlorobenzene and then with water and dried. 34.2 g of 93% strength by weight 1-nitroanthraquinone are obtained. The content of 1,5-dinitroanthraquinone is 1.7% by weight and that of anthraquinone is 0.25% by weight.

EXAMPLE 9

50 G of crude 1-nitroanthraquinone are stirred with 20 g of sodium sulphite and 400 ml of water for 6 hours in an autoclave at 105°C. After cooling to about 90°C, 200 ml of chlorobenzene are added and the mixture is stirred for a further 4 hours at about 93°C under reflux conditions and at normal pressure. It is cooled to 45°C, the precipitate is filtered off at this temperature and the filter cake is thoroughly pressed out and rinsed with water. The yield of dry material is 27.3 g of 98% strength by weight 1-nitroanthraquinone. The content of 1,5-dinitroanthraquinone is 0.9% by weight. Including the 1-nitroanthraquinone which has remained in the chlorobenzene mother liquor, the total yield is calculated to be 64% of theory relative to anthraquinone.

EXAMPLE 10

50 G of crude 1-nitroanthraquinone are stirred with 20 g of sodium sulphite and 400 ml of water for 6 hours in an autoclave at 105°C. After cooling to about 80°C, 200 ml of toluene are added and the mixture is stirred for a further 4 hours at about 84°C under reflux conditions at normal pressure. After adding a little di-sec.-butylnaphthalenesulphonate, the mixture is cooled to 45°C and allowed to settle out, and the aqueous suspension by itself is filtered on a suction filter. After washing and drying, 30.1 g of 97% strength by weight 1-nitroanthraquinone are isolated, having a residual content of 1,5-dinitroanthraquinone of 1.1% by weight. The total yield, including the 1-nitroanthraquinone which has remained in the toluene phase, is 64% of theory relative to anthraquinone employed.

EXAMPLE 11

50 G of crude 1-nitroanthraquinone containing 77% of 1-nitroanthraquinone and about 12% of dinitroanthraquinone are heated with 200 ml of toluene to 150°C for 1 hour in a glass autoclave. The mixture is then cooled to 100°C, a solution of 20 g of sodium sulphite and 1 g of di-sec.-butylnaphthalenesulphonate in 400 ml of water is pumped in, and the mixture is stirred for a further 10 hours at 100°C. It is cooled to 60°C, and after brief settling-out, the toluene phase is siphoned off. The aqueous suspension is filtered and the filter residue is washed with water and dried. The yield is 33.5 g and the content of 1-nitroanthraquinone is 97% by weight.

EXAMPLE 12

50 g of crude 1-nitroanthraquinone are stirred with 200 ml of chlorobenzene for 1 hour at 130°C in an autoclave. A solution of 15 g of sodium sulphite in 400 ml of water is then pumped in at 130°C over the course of 1 hour and the mixture is stirred for a further 6 hours at 105°C. It is allowed to cool to 20°C and the precipitate is filtered off and washed with chlorobenzene and then with water. After drying, 22.8 g of 99% strength by weight 1-nitroanthraquinone are isolated, having a residual content of, in total, less than 0.5% by weight of dinitroanthraquinone (compare Table A).

EXAMPLES 13 – 29

The examples indicated in Table B which follows were carried out in fundamentally the same manner. 50 g of a crude 1-nitroanthraquinone manufactured as in Example 1 were stirred for 6 hours, in an autoclave at 105°C, with the amount of sodium sulphite indicated in column I, with the volume indicated in column II of the solvent noted in column III, and with 400 ml of water. The organic solvent was then distilled off azeotropically under normal pressure, with the volume of the aqueous phase being adjusted to about 600 ml by adding water. Finally, the aqueous suspension was filtered hot and the product was rinsed with hot water and dried. The yield (relative to 1-nitroanthraquinone employed) and the content of the various dinitroanthraquinones and hydroxynitroanthraquinones in the 1-nitroanthraquinone are shown in columns IV—IX.

Table B

| Example No. | I | II | III | IV | V | VI | VII | VIII | IX |
|---|---|---|---|---|---|---|---|---|---|
| 13 | 15 | 200 | Chlorobenzene | 1.0 | 0.3 | 0.2 | 0.1 | 0.1 | 92 |
| 14 | 15 | 200 | Toluene | 1.4 | 0.2 | 0.2 | 0.1 | 0.3 | 91 |
| 15 | 15 | 200 | O-Xylene | 1.6 | 0.3 | 0.3 | 0.1 | 0.4 | 95 |
| 16 | 15 | 200 | Cumene | 1.7 | 0.3 | 0.3 | 0.3 | 0.5 | 95 |
| 17 | 15 | 200 | Tetralin | 1.7 | 0.3 | 0.3 | 0.3 | 0.6 | 97 |
| 18 | 15 | 200 | Isododecylbenzene | 1.7 | 0.3 | 0.3 | 0.3 | 0.6 | 97 |
| 19 | 15 | 200 | p-Chlorotoluene | 1.7 | 0.3 | 0.3 | 0.1 | 0.6 | 92 |
| 20* | 15 | 200 | o-Dichlorobenzene | 1.8 | 0.6 | 0.5 | 0.5 | 0.1 | 97 |
| 21* | 15 | 200 | Nitrobenzene | 1.9 | 0.5 | 0.5 | 0.9 | <0.1 | 80 |
| 22 | 15 | 200 | Anisole | 1.9 | 0.7 | 0.5 | 0.3 | 0.1 | 91 |
| 23 | 15 | 200 | Dioxane | 1.7 | 0.2 | 0.2 | 0.5 | 0.1 | 82 |
| 24 | 15 | 200 | Dibutyl ether | 2.0 | 0.4 | 0.4 | 0.5 | 0.7 | 94 |
| 25 | 15 | 200 | Methyl glycol | 2.3 | 0.3 | 0.3 | 0.8 | 0.7 | 89 |
| 26 | 15 | 200 | Cyclohexanol | 2.3 | 0.6 | 0.5 | 0.8 | 0.6 | 92 |
| 27 | 20 | 1 | Chlorobenzene | 2.2 | 0.6 | 0.6 | 0.8 | 0.9 | 84 |
| 28 | 20 | 2.5 | Chlorobenzene | 1.7 | 0.5 | 0.4 | 0.5 | 0.7 | 86 |
| 29 | 20 | 5 | Chlorobenzene | 1.5 | 0.5 | 0.3 | 0.5 | 0.7 | 86 |

*Solvent distilled off in vacuo.
I = g of $Na_2SO_3$
II = ml
III = organic solvent
IV = % by weight of 1,5-dinitroanthraquinone
V = % by weight of 1,6-dinitroanthraquinone
VI = % by weight of 1,7-dinitroanthraquinone
VII = % by weight of 1,8-dinitroanthraquinone
VIII = % by weight of hydroxynitroanthraquinones
IX = yield, % of theory.

EXAMPLE 30

A suspension of 250 g of anthraquinone in 200 ml of methylene chloride and 68.4 ml of 98% strength by weight nitric acid is nitrated over the course of about 3 hours at the reflux temperature by adding 85.0 ml of 100% strength by weight sulphuric acid, and the mixture is stirred for a further 4 hours at this temperature. The batch is then poured into 2 l of water, the pH is adjusted to 7–8 by adding concentrated sodium hydroxide solution, and the methylene chloride is distilled off. The suspension is heated with 600 ml of chlorobenzene to 100°C and a concentrated solution of 120 g of sodium sulphite in water is pumped in. After 6 hours' reaction time at 100°C, the mixture is cooled to 60°C and is filtered and the product is washed first with 400 ml of chlorobenzene and then with water until the latter is clear. After drying, 223 g are obtained, containing 97% by weight of 1-nitroanthraquinone, corresponding to 71% of theory. The total yield, including the 1-nitroanthraquinone dissolved in the mother liquor, is 75% of theory (compare Table A).

EXAMPLE 31

50 G of crude 1-nitroanthraquinone are stirred for 6 hours at 105°C with 15 g of sodium sulphite, 400 ml of water, 150 ml of toluene and 0.5 g of di-sec.-butyl naphthalenesulphonate. The mixture is cooled to 80°C, the toluene phase is siphoned off, and a solution of 45 g of sodium sulphide in 300 ml of water is pumped in. The mixture is stirred for a further hour at 100°C and the precipitate of 1-aminoanthraquinone is then filtered off hot. After washing and drying, 30.9 g, containing 92% by weight of 1-aminoanthraquinone are obtained. This 1-aminoanthraquinone contains less than 2% by weight of diaminoanthraquinones and can be reacted further in accordance with the known industrial processes, for example by sulphobromination to give so-called bromamine-acid.

EXAMPLE 32

100 g of pre-purified 1-nitroanthraquinone of the following composition: 84% by weight of 1-nitroanthraquinone, 0.5% by weight of 2-nitroanthraquinone, 3% by weight of 1,5-dinitroanthraquinone, 5% of 1,6-dinitroanthraquinone, 4% of 1,7-dinitroanthraquinone and 3% of 1,8-dinitroanthraquinone, 30 g of sodium sulphite, 0.5 g of di-sec.-butyl naphthalenesulphonate and 800 ml of water are stirred together for 6 hours at 100°C. The reaction temperature is then lowered to about 90°C, 200 ml of chlorobenzene are added and the mixture is stirred for a further 4 hours at this temperature. It is cooled to 20°C and the precipitate is filtered off and washed with water until the latter is clear. The yield is 78.8 g of 98% strength by weight 1-nitroanthraquinone, corresponding to 92% of theory. The 1-nitroanthraquinone contains less than 0.25% by weight of anthraquinone and 2-nitroanthraquinone and only 0.6% by weight of 1,5-dinitroanthraquinone in addition to 0.3% of 1,6-dinitroanthraquinone, 0.2% of 1,7-dinitroanthraquinone and 0.3% of 1,8-dinitroanthraquinone. Taking into account the 1-nitroanthraquinone dissolved in the mother liquor, the total yield is 95% of theory.

EXAMPLE 33

50 g of crude 1-nitroanthraquinone from an anthraquinone nitration with approx. 95% conversion of the anthraquinone (approx. 5% of anthraquinone, 76% of 1-nitroanthraquinone and 11% of dinitroanthraquinone) are stirred with 15 g of sodium sulphite, 200 ml of chlorobenzene and 400 ml of water for 6 hours at 105°C. 100 ml of chlorobenzene are then distilled off and the precipitate is filtered off at 60°C. After washing with chlorobenzene and water, and drying, 32.1 g of 1-nitroanthraquinone, containing 98% by weight of 1-nitroanthraquinone, are isolated. The residual contents of by-products are 0.5% of anthraquinone, 0.25% of 2-nitroanthraquinone and 0.8% of 1,5-dinitroanthraquinone, as well as 0.2% each of 1,6-, 1,7- and 1,8-dinitroanthraquinone.

EXAMPLE 34

50 g of a crude 1-nitroanthraquinone manufactured according to Example 1 are stirred with 20 g of sodium sulphite in 400 ml of water for 6 hours at the reflux temperature. After filtration, washing and drying, 38.2 g of 1-nitroanthraquinone of the composition indicated in Table A are obtained (= 69% of theory, relative to anthraquinone employed).

We claim:

1. In a process wherein a reaction mixture obtained by the nitration of anthraquinone and comprising 1-nitroanthraquinone and containing dinitroanthraquinone as an impurity is treated at temperatures of 75°C–150°C with an aqueous solution of a salt of sulfurous acid to solubilize said dinitroanthraquinone and the solubilized dinitroanthraquinone is removed from said 1-nitroanthraquinone the improvement which comprises conducting the treatment in the presence of an inert organic solvent selected from the group consisting of aromatic and araliphatic hydrocarbons of the benzene and naphthalene series with up to thirty carbon atoms which may contain in the nucleus halogen, nitro, sulphone, ether, thioether, keto or carbalkoxy groups or mixtures thereof or aliphatic and alicyclic hydrocarbons with up to thirty carbon atoms which may contain halogen, nitro, sulphone, sulfoxide, ether, thioether, hydroxyl, carbonyl, carboxyl, carboalkoxy, or carboaryloxy groups or mixtures thereof.

2. Process according to claim 1, characterised in that per part by weight of 1-nitroanthraquinone containing dinitroanthraquinone, 0.01 – 40 parts by volume of organic solvent are employed.

3. Process of claim 2 wherein 0.1–10 parts by volume of organic solvent are employed.

4. Process according to claim 1, characterised in that it is carried out at pH-values above 8.

5. Process of claim 4, wherein the pH is from 9–12.

6. Process of claim 1 wherein the temperature is 80°–130°C.

7. Process according to claim 1, characterised in that water-immiscible organic solvents are used.

8. Process according to claim 7, characterised in that aromatic or aliphatic optionally halogenated hydrocarbons are used.

9. Process according to claim 8, characterised in that benzene, toluene, xylene, cumene, chlorobenzene, chlorotoluene or dichlorobenzene are used.

* * * * *